United States Patent
Aher et al.

(10) Patent No.: US 9,266,854 B2
(45) Date of Patent: Feb. 23, 2016

(54) ONE STEP PROCESS FOR SYNTHESIS OF CYCLIC CARBONATES

(71) Applicant: Council of Scientific & Industrial Research, New Delhi (IN)

(72) Inventors: Ravindra Dattatray Aher, Maharashtra (IN); Boopathi Senthil Kumar, Maharashtra (IN); Arumugam Sudalai, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/434,216

(22) PCT Filed: Oct. 8, 2013

(86) PCT No.: PCT/IN2013/000610
§ 371 (c)(1),
(2) Date: Apr. 8, 2015

(87) PCT Pub. No.: WO2014/057500
PCT Pub. Date: Apr. 17, 2014

(65) Prior Publication Data
US 2015/0259318 A1      Sep. 17, 2015

(30) Foreign Application Priority Data
Oct. 8, 2012   (IN) .............. 3143/DEL/2012

(51) Int. Cl.
*C07D 317/54*   (2006.01)
*C07D 317/36*   (2006.01)

(52) U.S. Cl.
CPC ............ *C07D 317/54* (2013.01); *C07D 317/36* (2013.01)

(58) Field of Classification Search
CPC ...................................................... C07D 317/54
USPC ......................................................... 549/230
See application file for complete search history.

(56) References Cited

PUBLICATIONS

Aher et al., "One-pot synthesis of cyclic carbonates from aldehydes, sulfurylide and C02", SYNLETT, 25(7):97-101, Nov. 7, 2013.
Sakakura et al., "Transformation of carbon dioxide", Chemical Reviews, American Society, US, 107(6):2365-2387, Jun. 1, 2007.
Yan et al., "One approach to cyclic carbonates via a three-component cyclisation of the phenacyl bromide, C02 and aldehyde", Journal of Organic Chemistry, 76:2459-2464, Apr. 15, 2011.
European Patent Office, International Search Report and Written Opinion for International Patent Application No. PCT/IN2013/000610, dated Jan. 14, 2014.

*Primary Examiner* — Taofiq A Solola
(74) *Attorney, Agent, or Firm* — Fish & Richardson P.C.

(57) ABSTRACT

This invention discloses one step transition metal free process for synthesis of cyclic carbonates from aldehydes and carbon dioxide. More particularly, the invention relates to single step procedure involving Corey-Chaykovsky reaction and in-situ $CO_2$ insertion.

8 Claims, No Drawings

ONE STEP PROCESS FOR SYNTHESIS OF CYCLIC CARBONATES

FIELD OF THE INVENTION

This invention relates to one step transition metal free process for synthesis of cyclic carbonates from aldehydes and carbon dioxide. More particularly, the invention relates to single step procedure involving Corey-Chaykovsky reaction and in-situ $CO_2$ insertion.

BACKGROUND AND PRIOR ART

The global warming resulted from increased consumption of fossil fuel is becoming an important environmental issue today. Therefore, it is crucial to use the greenhouse gas ($CO_2$) constructively, after separation from its emission source, to reduce greenhouse effect/global warming as well as to synthesize variety of organic products.

Cycloaddition of $CO_2$ with epoxides to produce cyclic carbonates (e.g., ethylene carbonate and propylene carbonate) is one of a few industrial synthetic processes that utilize $CO_2$ as a raw material. Cyclic carbonates are widely used as electrolyte components in lithium ion batteries, polar solvents, and intermediates in the production of pharmaceuticals and fine chemicals.

There is ample literature available on synthesis of organic carbonates from $CO_2$ as it is a very attractive method. The research is progressed in this direction because, using $CO_2$ as an abundant and renewable carbon source, also avoids the use of toxic and environmentally harmful phosgene. The organic carbonates, especially cyclic carbonates, are commercially important; whose usefulness permits their applications in several fields of the chemical and pharmaceutical industry, such as manufacturing of engineering plastics, electrolyte solvents for lithium ion batteries, organic solvents, green reagents, and fuel additives etc. In literature cyclic carbonates are synthesized by using epoxides, diols and olefins as starting material using toxic and expensive metal catalyst under harsh reaction conditions.

An article titled "Synthesis of cyclic carbonates from epoxide and $CO_2$" by Michael North, Riccardo Pasquale and Carl Young published in Green Chemistry Issue 9, 2010, discloses synthesis of cyclic carbonates from epoxides and $CO_2$ in presence of a catalyst, as shown below:

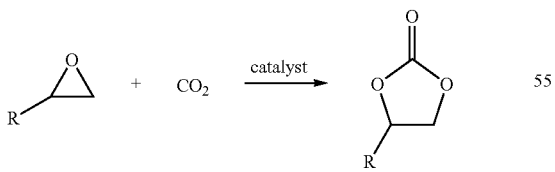

Another article titled "Efficient synthesis of cyclic carbonates from $CO_2$ and epoxides over cellulose/KI by Shuguang Liang, et al. in Chem. Commun., 2011, 47, 2131-2133, discloses cellulose/KI as a very active, selective, stable, and recyclable catalyst for the cycloaddition reactions of $CO_2$ and epoxides due to the excellent synergetic effect of cellulose and KI. The reaction is as shown below:

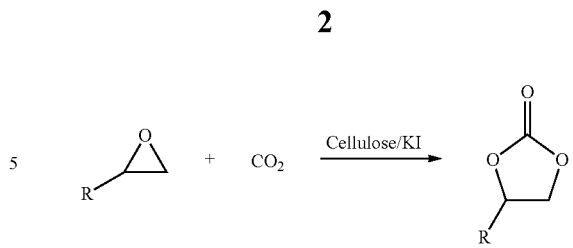

Another article titled "Synthesis of cyclic carbonates uses monometallic and helical bimetallic, aluminium complexes" by Jose A. Castro-Osma et al in Catal. Sci. Technol., 2012, 2, 1021-1026, investigated the use of aluminium complexes of a series of bis(pyrazol-1-yl)methane derived ligands as catalysts for the synthesis of cyclic carbonates from carbon dioxide and epoxides and found that a bimetallic, helical, heteroscorpionate complex displayed significantly higher catalytic activity than the corresponding monometallic complexes, as shown below:

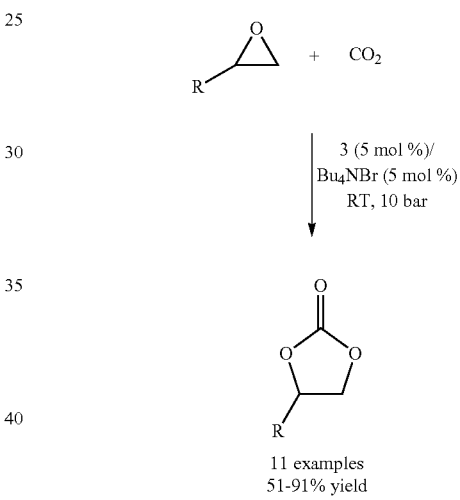

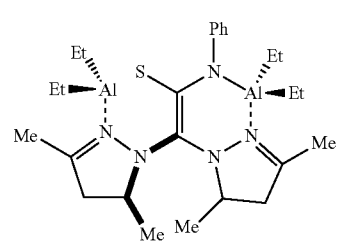

Yet another article titled "Conversion of carbon dioxide and olefins into cyclic carbonates in water" by Nicolas Eghbali and Chao-Jun Li in Green Chem., 2007, 9, 213-215, discloses a method to convert alkenes and $CO_2$ into cyclic carbonates directly in water by using N-bromosuccinimide (NBS) together with 1,8-diazabicyclo[5.4.0]undecenc-7-ene (DBU) in water, or by using a catalytic amount of bromide ion together with aqueous $H_2O_2$ as shown below.

Synthesis of a Cyclic Carbonate from an Olefin

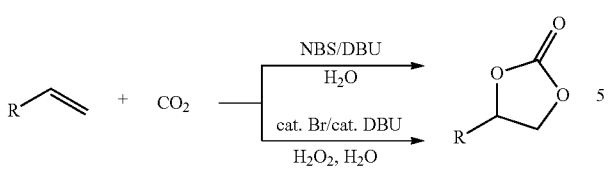

An article entitled "transformation of $CO_2$" by Sakakura in Chem review, 2007, 107, 2365-2387, wherein, over view on synthesis of cyclic carbonates is discussed as per the schemes below:

Synthesis of a Cyclic Carbonate from an Olefin

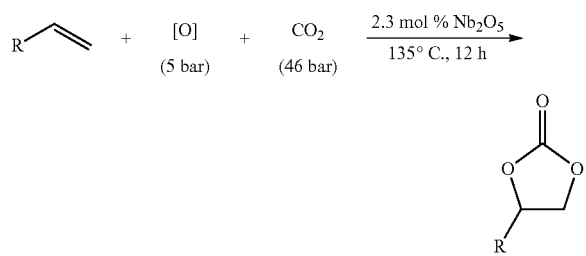

Synthesis of a Cyclic Carbonate from a Diol

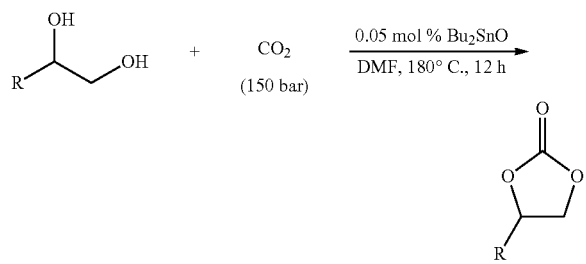

Synthesis of a Cyclic Carbonate from a Cyclicketal

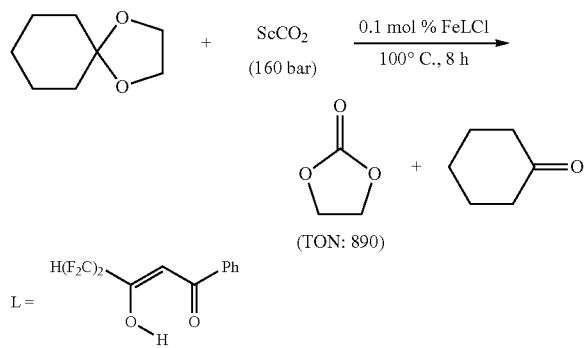

Synthesis of a Cyclic Carbonate from a Propargyl Carbonate

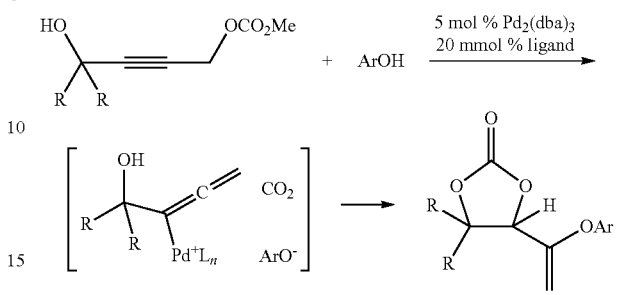

Article titled, "Synthesis of cyclic carbonates from epoxides and carbon dioxide using bimetallic aluminium (salen) complexes" by Michael North in ARKIVOC 2012 (i) 610-628 reports a class of bimetallic, aluminium based catalysts for the synthesis of cyclic carbonates (including all the commercially important cyclic carbonates) which are active under exceptionally mild reaction conditions. Batch reactions can be carried out at ambient temperature and one bar carbon dioxide pressure whilst continuous flow reactions can be carried out at 100° C. using catalysts immobilized on amorphous silica. The catalysts have been shown to be compatible with waste carbon dioxide such as that present in unpurified flue-gas. The cost of production of the catalysts has been analyzed and routes for their synthesis developed to minimize the cost of their production.

Article titled, "Selectivity of the cyclic carbonate formation by fixation of carbon dioxide into epoxides catalyzed by Lewis bases" by C. R. Gomes et al. in Tetrahedron Letters 49 (2008) 6879-6881 reports Cyclic carbonate and polycarbonate have been selectively obtained with good conversion by coupling carbon dioxide with diglycidylether of bisphenol A. The ruthenium trichloride supported on tetraethylammonium bromide and polyphosphotungstic acid has been found active and selective to produce the corresponding monomeric and polymeric carbonates. These catalysts can be recycled keeping their high product conversion and selectivity. The heteropolyacid itself showed high activity also under supercritical CO2 conditions to yield polycarbonate.

Article titled, "Synthesis of Cyclic Carbonates from CO2 and Diols via Electrogenerated N-Heterocyclic Carbenes" by La-Xia Wu, Huan Wang, Zhuo-Ying Tu, Bin-Bin Ding, Yan Xiao, Jia-Xing Lu in Int. J. Electrochem. Sci., Vol. 7, 2012 reports Synthesis of cyclic carbonates has been achieved from CO2 and diols in room temperature ionic liquids (RTILs) via electrogenerated N-heterocyclic carbenes with good yields. Only mild reaction conditions of 40° C. temperature and 1 atm CO2 were used.

Article titled, "Catalytic Processes for Chemical Conversion of Carbon Dioxide into Cyclic Carbonates and Polycarbonates" by Cheng-Xia Miao, Jin-Quan Wang and Liang-Nian He in The Open Organic Chemistry Journal, 2008; 2, 68-82 the synthesis of polycarbonates or cyclic carbonates catalyzed by metal salen complexes through adjusting the architecture of the ligands and optimizing reaction conditions, such as temperature, pressure, co-catalysts, epoxide concentration. Furthermore, the recent progress for the synthesis of cyclic carbonates via the coupling reactions of epoxides and CO2 mediated by both homogeneous and heterogeneous catalysts is particularly reviewed.

Article titled, "Efficient synthesis of cyclic carbonate from carbon dioxide catalyzed by polyoxometalate: the remarkable effects of metal substitution" by Hiroyuki Yasuda, Liang-Nian He, Toshiyasu Sakakura, Changwen Hu in Journal of Catalysis 233 (2005) 119-122 reports Tetraalkylammonium salts of transition-metal-substituted polyoxometalates, such as [(n-C7H15)4N]6 [α-SiW11O39Co] and [(n-C7H15)4N]6 [α-SiW11O39Mn], efficiently catalyze cyclic carbonate synthesis from carbon dioxide and epoxide. The catalytic activity is significantly influenced by the type of transition metal and the countercation (Co2+=Mn2+>Ni2+>Fe3+Cu2+; (n-C7H15)4N+>(n-C4H9)4N+K+). Co- or Mn-substituted catalysts required neither additional organic solvents nor additives. Thus, polyoxometalates are promising as non-halogen anionic components of catalysts for cyclic carbonate synthesis.

U.S. Pat. No. 6,924,379 B2 patent discloses A catalytic system comprising of Zinc-substituted polyoxometalate, Nal2[WZn3(H2O)2(ZnW9O34)2].48H2O and a Lewis base has been discovered to be efficient for chemical fixation of CO2 With epoxides to form cyclic carbonates.

U.S. Pat. No. 6,870,004 B1 patent discloses Salen complexes were found to be excellent catalysts for the reaction of terminal epoxides With CO2 when used in conjunction with a Lewis base cocatalyst (DMAP). This catalyst system cleanly affords the product cyclic carbonates in high yield under mild reaction conditions and is applicable to a variety of terminal epoxides.

US 2006/0094893 A1 patent relates to a process for the preparation of cyclic carbonates comprising contacting an epoxide With CO2 in the presence of a titanosilicate catalyst and a base co-catalyst at a temperature above 313 K and a pressure above 2 bar for a period of 0.5 to 8 hrs and isolating the formed cyclic carbonate from the reaction mixture by conventional methods.

U.S. Pat. No. 7,365,214 B2 patent discloses an improved process for the preparation of cyclic carbonates which comprises reacting an olefins or its epoxide with carbon dioxide or a mixture of oxygen-containing compound and carbon dioxide, in the presence of Zeolite-based catalyst and a Lewis base co catalyst, at a minimum pressure of 30 psig and temperature between 40 to 120° C. for 0.5 to 4 hrs., separating the catalyst and recovering the corresponding cyclic carbonate formed by conventional methods.

WO 2011159219 A1 patent discloses a process for production of a cycloaliphatic carbonate from a diol, triol or polyol and a carbon dioxide source, such as a dialkyl carbonate. Said process is performed in a solvent-free medium using a N-heterocyclic carbene or N-heterocyclic carbene complex as catalyst. Said N-heterocyclic carbene or carbene complex is preferably attached to a lipase. Said process comprises preferably a transesterification step and a thermal disproportionation step and yielded cycloaliphatic carbonate is in preferred embodiments a monocyclic carbonate having a five-membered or a six-membered ring.

As detailed above, a lot of catalyst systems have been developed in the past for fixation of $CO_2$, especially to prepare cyclic carbonates, high temperature and pressure are often required. The main reason for this is the carbon atom in $CO_2$ is in its most oxidized form and is therefore relatively unreactive. A large input of energy is required to transform $CO_2$.

From the above, it is evident that the industrial production of carbonates is not green because methods for production of linear carbonates rely on phosgene and those of cyclic carbonates rely on propylene oxide/oxiranes. Thus most reported protocols use toxic and expensive metal catalysts, requires relatively high pressure, high temperature, and long reaction time coupled with tedious workup for separation and produce environmentally harmful side products.

Further, in case of use of metal catalyst there will be issues like toxicity as well as separation of heavy metal, which increases the number of steps. Another disadvantage comes with handling of Phosgene, which is difficult to handle. Therefore, there is an increasing demand for cyclic carbonates synthesis in an environmentally benign process.

OBJECT OF INVENTION

The main objective of the present invention is to provide one step transition metal free process for synthesis of cyclic carbonates from aldehydes and carbon dioxide.

Another objective of the present invention is to provide single step procedure involving Corey-Chaykovsky reaction and in-situ $CO_2$ insertion.

SUMMARY OF INVENTION

Accordingly, the present invention provides one step transition metal free process for the synthesis of cyclic carbonates of formula I from an aldehyde of formula II and Corey-Chaykovsky reagent in presence of carbon dioxide comprising:

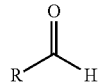

Formula II

R = alkyl, aryl, vinyl

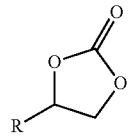

Formula I

R = alkyl, aryl, vinyl a. adding a solvent to NaH followed by stirring under nitrogen at temperature ranging between 0-35° C. for a period ranging between 0.5 to 1 hrs obtain a slurry;
b. adding Corey Chaykovsky reagent to the slurry of step (a) to obtain a homogeneous solution;
c. adding aldehyde of formula II slowly to homogenous mixture of step (b) followed by bubbling $CO_2$ gas into the reaction mixture with stirring at temperature ranging between 40 to 60° C. for a period ranging between 6 to 8 hrs to obtain cyclic carbonate of formula I.

In an embodiment of the present invention the Corey-Chaykovsky reagent used in step (b) is selected from sulfurylide.

In one embodiment of the present invention the Corey-Chaykovsky reagent is preferably selected from $Me_3SI$ or $Me_3SOI$.

In another embodiment of the present invention NaH used in step (a) was previously washed with petroleum ether to remove mineral oil.

Still in another embodiment of the present invention the solvent used in step (a) is selected from DMSO or a mixture of DMSO and THF.

Still in another embodiment of the present invention the solvent is preferably mixture of DMSO and THF in the ratio of 1:1. The process according to claim 1, wherein representative compounds of cyclic carbonate of formula I are
i. 4-Phenyl-1,3-dioxolan-2-one
ii. 4-(2-bromophenyl)-1,3-dioxolan-2-one
iii. 4-(4-fluorophenyl)-1,3-dioxolan-2-one
iv. 4-(4-chlorophenyl)-1,3-dioxolan-2-one
v. 4-(4-(trifluoromethyl)phenyl)-1,3-dioxolan-2-one
vi. 4-Phenyl-1,3-dioxolan-2-one
vii. 4-(2-bromophenyl)-1,3-dioxolan-2-one
viii. 4-(4-fluorophenyl)-1,3-dioxolan-2-one
ix. 4-(4-chlorophenyl)-1,3-dioxolan-2-one
x. 4-(4-(trifluoromethyl)phenyl)-1,3-dioxolan-2-one
xi. 4-(2-methoxyphenyl)-1,3-dioxolan-2-one
xii. 4-(2-nitrophenyl)-1,3-dioxolan-2-one
xiii. 4-(3-nitrophenyl)-1,3-dioxolan-2-one
xiv. 4-(benzo[d][1,3]dioxol-5-yl)-1,3-dioxolan-2-one
xv. 4-(3,4,5-trimethoxyphenyl)-1,3-dioxolan-2-one
xvi. 4,5-dimethoxy-2-(2-oxo-1,3-dioxolan-4-yl)benzonitrile
xvii. (E)-4-styryl-1,3-dioxolan-2-one
xviii. 4-phenethyl-1,3-dioxolan-2-one
xix. tert-butyl ((S)-1-((S)-2-oxo-1,3-dioxolan-4-yl)-2-phenylethyl)carbamate
xx. 4-(2-(benzyloxy)ethyl)-1,3-dioxolan-2-one
xxi. 4-vinyl-1,3-dioxolan-2-one
xxii. 4-ethyl-1,3-dioxolan-2-one
xxiii. 4-methyl-1,3-dioxolan-2-one
xxiv. 4-isopropyl-1,3-dioxolan-2-one
xxv. 4-butyl-1,3-dioxolan-2-on
xxvi. 4-hexyl-1,3-dioxolan-2-one Still in another embodiment of the present invention yield of cyclic carbonate of formula I is in the range of 40-98%.

DESCRIPTION OF THE INVENTION

In accordance with the above, the instant invention discloses an effective single step synthesis for preparation of cyclic carbonates involving Corey-Chaykovsky reaction and in-situ $CO_2$ insertion into aldehyde system.

The invention provides a cheaper and practical protocol for the synthesis of a wide variety of aromatic and aliphatic cyclic carbonates that proceeds via in situ opening of epoxides with good yields in a single step using $Me_3SI$ or $Me_3SOI/NaH$ as a reagent and carbon dioxide as C1- source, from commercially available aldehydes.

In an embodiment the present invention provides a single step synthesis for the preparation of cyclic carbonates of formula I using aldehydes of formula II via Corey Chaykovsky reaction, comprising:
a. adding solvent to NaH (previously washed with petroleum ether to remove mineral oil) followed by stirring under nitrogen to obtain a slurry;
b. adding Corey Chaykovsky reagent to the slurry of step (a) to obtain a homogeneous solution;
c. adding aldehyde of formula II slowly to homogenous mixture of step (b)
d. bubbling $CO_2$ gas into the reaction mixture of step (c) with stirring followed by work-up and purification affords the desired product of formula I.

The single step synthesis for the preparation cyclic carbonates of formula I is shown below in Scheme 1:

Scheme 1: Synthesis of cyclic carbonates from aldehydes

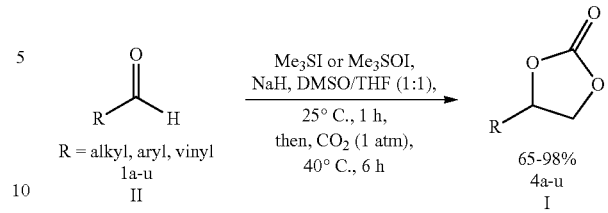

R = alkyl, aryl, vinyl
1a-u
II 65-98%
4a-u
I

Wherein R is selected from alkyl, aryl or vinyl.

In a preferred embodiment, the present invention provides a single step synthesis for the preparation of cyclic carbonates of formula I wherein the Corey Chaykovsky reagent is selected from sulfur ylide and is preferably selected from $Me_3SI$ or $Me_3SOI$.

In another preferred embodiment the present invention provides a single step synthesis, wherein the solvent is selected from DMSO or a mixed solvent system of DMSO and THF and is preferably a mixed solvent system of DMSO and THF in the ratio of 1:1.

In yet another preferred embodiment, the present, invention discloses Corey's reaction on benzaldehyde at 25° C. and in situ generated epoxide was converted to corresponding cyclic carbonate (yield: >93%) by utilizing $CO_2$ (1 atm) at 40° C.

In preferred embodiment, the present invention provides the optimization studies involving benzaldehyde, sulfur ylide and $CO_2$ as shown below in table 1:

TABLE 1

Optimization studies involving benzaldehyde, sulfur ylide and $CO_2$[a]

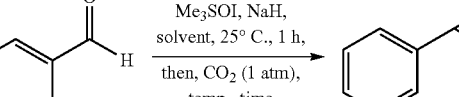

| entry | solvent | temp. (° C.) | time (h) | yield (%)[b] 2a | 3a | 4a |
|---|---|---|---|---|---|---|
| 1 | DMSO | 25 | 12 | 95 | — | — |
| 2 | DMSO | 40 | 12 | — | 65 | 30 |
| 3 | DMSO | 60 | 12 | — | 53 | 41 |
| 4 | DMSO | 80 | 12 | — | 23 | 71 |
| 5 | DMSO/THF(1:1) | 40 | 6 | — | — | 96 |

[a]Reaction conditions: aldehyde (3 mmol), NaH (3.3 mmol), $Me_3SOI$ (3.3 mmol), solvent (20 mL);
[b]Isolated yield after column chromatographic purification;

In another embodiment, the present invention provides the substrate scope and general validity of the reaction by employing a variety of aromatic and aliphatic aldehydes under the same reaction conditions; and the excellent yields as shown below in table 2:

TABLE 2

Substrate scope of aldehyde for cyclic carbonate synthesis

| entry | aldehydes | Yield of 4a-k (%)[b] |
|---|---|---|
| 1 | benzaldehyde (1a) | 96 |
| 2 | acetaldehyde (1b) | 40 |
| 3 | propionaldehyde (1c) | 65 |
| 4 | isobutyraldehyde (1d) | 73 |
| 5 | n-pentanal (1e) | 89 |
| 6 | n-heptanal (1f) | 94 |
| 7 | acrolein (1g) | 65 |
| 8 | cinnamaldehyde (1h) | 98 |
| 9 | 2-OMe-benzaldehyde (1i) | 85 |
| 10 | 3,4,5-(OMe)$_3$-benzaldehyde (1j) | 90 |
| 11 | 4-F- benzaldehyde (1k) | 90 |

| entry | aldehydes | Yield of 4l-u (%)[b] |
|---|---|---|
| 12 | 4-Cl- benzaldehyde (1l) | 87 |
| 13 | 2-Br- benzaldehyde (1m) | 96 |
| 14 | 4-CF$_3$- benzaldehyde (1n) | 98 |
| 15 | 2-NO$_2$- benzaldehyde (1o) | 79 |
| 16 | 3-NO$_2$- benzaldehyde (1p) | 75 |
| 17 | piperonal (1q) | 86 |
| 18 | 3-benzyloxy-1-propanal (1r) | 80 |
| 19 | 3-phenylpropanal (1s) | 77 |
| 20 | 3,4-(OMe)$_2$-2-CN-phenylpropanal (1t) | 83 |
| 21 | (S)-(α-NHBoc)- 3-phenylpropanal (1u) | 79 |

[a]Reaction conditions: aldehyde (3 mmol), NaH (3.6 mmol), Me$_3$SOI (3.9 mmol), DMSO (10 mL), THF (10 mL), 25° C., 1 h, then CO$_2$ bubbling 40° C., 6 h.
[b]Isolated yield after chromatographic purification over silica gel (100-200 mesh) using petroleum ether/EtOAc.

Thus the single step method for the preparation of cyclic carbonate derivatives according to the invention produces preparative yields from a variety of aliphatic and aromatic aldehydes with both electron-donating and withdrawing groups present on aromatic ring.

EXAMPLES

The following examples are given by way of illustration and therefore should not be construed to limit the scope of the present invention.

Example 1

General experimental procedure for the synthesis of cyclic NaH (6:6 mmol) (previously washed with petroleum ether to remove mineral oil) was taken in an oven dried three naked round bottom flask, followed by addition of mix of DMSO and THF (1:1) (15 mL) through a septum to it and the whole slurry was stirred at 25° C. under nitrogen. Then trimethylsulfoxonium iodide (6.6 mmol) was added to the slurry over a period of 5 minutes via a solid addition funnel until it becomes a homogeneous solution. After 15 minutes, aldehyde (6 mmol, dissolved in 5 mL of THF) was added slowly to reaction mixture. After complete conversion of aldehyde to epoxide (confirmed by TLC), CO$_2$ gas was bubbled into the reaction mixture and stirring was continued at 40° C. for 6 hours. Water 30 mL was added to quench reaction mixture and then extracted with ethyl acetate (30 mL×3), organic layer washed with brine, dried over sodium sulfate and concentrated on rotavapour to obtain phenyl carbonate. The product was purified by silica gel column chromatography using pet ether and ethyl acetate (8:2) as eluents.

Example 2

Spectroscopic Data of 4a-u

4-Phenyl-1,3-dioxolan-2-one (4a)

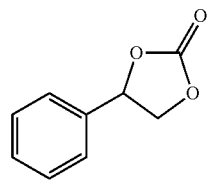 [SMILES: O=C1OCC(c2ccccc2)O1]

Yield: 96%; IR: (neat, cm$^{-1}$): u$_{max}$ 699, 716, 1002, 1068, 1168, 1211, 1458, 1813; $^1$H NMR (200 MHz, CDCl$_3$): δ 4.29 (t, J=7.9 Hz, 1H), 4.77 (t, J=7.9 Hz, 1H), 5.64 (t, J=7.9 Hz, 1H), 7.32-7.42 (m, 5H); $^{13}$C NMR (50 MHz, CDCl$_3$): δ 70.9, 77.8, 125.7, 129.0, 129.4, 135.8, 154.6; Elemental analysis: C$_9$H$_8$O$_3$, Calculated, C, 65.85; H, 4.91. Observed, C, 65.84; H, 4.90%.

4-(2-bromophenyl)-1,3-dioxolan-2-one (4m)

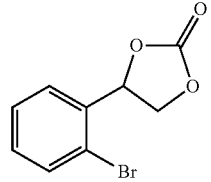 [SMILES: O=C1OCC(c2ccccc2Br)O1]

Yield: 96%; IR: (neat, cm$^{-1}$): u$_{max}$ 763, 969, 1072, 1125, 1159, 1208, 1473, 1817; $^1$H NMR (200 MHz, CDCl$_3$): δ 4.24 (dd, J=6.8, 1.7 Hz, 1H), 4.99 (t, J=8.4 Hz, 1H), 5.94 (t, J=8.0 Hz, 1H), 7.28-7.39 (m, 1H), 7.43-7.62 (m, 3H); $^{13}$C NMR (50 MHz, CDCl$_3$): δ 70.4, 76.3, 120.1, 126.0, 128.1, 130.4, 132.96, 136.3, 154.3; Elemental analysis: C$_9$H$_7$BrO$_3$, Calculated, C, 44.47; H, 2.90; Br, 32.87. Observed, C, 44.48; H, 2.89; Br, 32.88%.

4-(4-fluorophenyl)-1,3-dioxolan-2-one (4k)

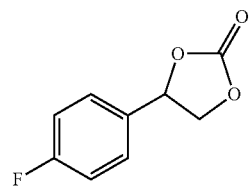 [SMILES: O=C1OCC(c2ccc(F)cc2)O1]

Yield: 90%; IR: (neat, cm$^{-1}$): u$_{max}$ 773, 840, 1069, 1161, 1210, 1385, 1514, 1818; $^1$H NMR (200 MHz, CDCl$_3$): δ 4.31

(t, J=8.2, 1H), 4.80 (t, J=8.3 Hz, 1H), 5.66 (t, J=8.0 Hz, 1H), 7.08-7.19 (m, 2H), 7.32-7.40 (m, 2H); $^{13}$C NMR (50 MHz, CDCl$_3$): δ 71.0, 77.3, 116, 116.5, 127.9, 128.0, 131.6, 154.4, 160.84; Elemental analysis: C$_9$H$_7$FO$_3$, Calculated, C, 59.35; H, 3.87; F, 10.43. Observed, C, 59.37; H, 3.86; F, 10.45%.

4-(4-(trifluoromethyl)phenyl)-1,3-dioxolan-2-one (4n)

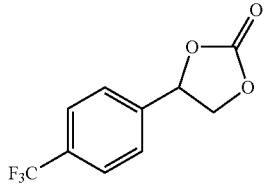 [SMILES: O=C1OCC(c2ccc(C(F)(F)F)cc2)O1]

Yield: 98%; IR: (neat, cm$^{-1}$): u$_{max}$ 771, 844, 1071, 1167, 1264, 1327, 1426, 1822; $^1$H NMR (200 MHz, CDCl$_3$): δ 4.30 (t, J=7.8, 1H), 4.85 (t, J=8.4 Hz, 1H), 5.74 (t, J=7.9 Hz, 1H), 7.48 (d, J=8.0 Hz, 1H), 7.32-7.40 (m, 2H); $^{13}$C NMR (50 MHz, CDCl$_3$): δ 70.8, 76.8, 120.9, 126.0, 126.2, 126.3, 126.4, 132.2, 139.9, 154.2;

4-(4-chlorophenyl)-1,3-dioxolan-2-one (4l)

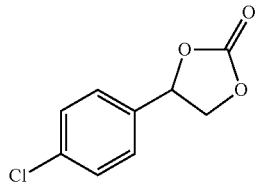 [SMILES: O=C1OCC(c2ccc(Cl)cc2)O1]

Yield: 87%; IR: (neat, cm$^{-1}$): u$_{max}$ 770, 829, 1071, 1167, 1384, 1494, 1816; $^1$H NMR (200 MHz, CDCl$_3$): δ 4.29 (t, J=8.4, 1H), 4.80 (t, J=8.4 Hz, 1H), 5.65 (t, J=7.8 Hz, 1H), 7.28-7.33 (m, 2H), 7.36-7.44 (m, 2H); $^{13}$C NMR (50 MHz, CDCl$_3$): δ 70.9, 77.1, 127.0, 129.4, 134.4, 135.7, 154.3; Elemental analysis: C$_9$H$_7$ClO$_3$, Calculated, C, 59.35; H, 3.87; Cl, 10.43. Observed, C, 59.37; H, 3.86; Cl, 10.45%.

4-(2-methoxyphenyl)-1,3-dioxolan-2-one (4i)

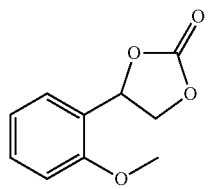

Yield: 85%; IR: (neat, cm$^{-1}$): u$_{max}$ 757, 1076, 1166, 1249, 1494, 1812; $^1$H NMR (200 MHz, CDCl$_3$): δ 3.85 (s, 3H), 4.25 (dd, J=8.4; 1.1 Hz, 1H), 4.81 (t, J=8.4 Hz, 1H), 5.81 (t, J=8.0 Hz, 1H), 6.89-7.03 (m, 2H), 7.31-7.38 (m, 2H); $^{13}$C NMR (50 MHz, CDCl$_3$): δ 55.4, 70.5, 74.7, 110.5, 120.9, 124.9, 126.1, 130.3, 154.9

4-(2-nitrophenyl)-1,3-dioxolan-2-one (4o)

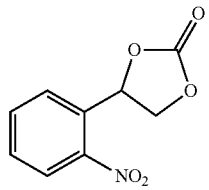 [SMILES: O=C1OCC(c2ccccc2[N+](=O)[O-])O1]

Yield: 79%; IR: (neat, cm$^{-1}$): u$_{max}$ 1073, 1167, 1350, 1527, 1819; $^1$H NMR (200 MHz, CDCl$_3$): δ 4.26 (dd, J=9.0, 3.3 Hz, 1H), 5.16 (t, J=8.9 Hz, 1H), 6.26 (dd, J=8.7, 2.7 Hz, 1H), (m, 1H), 7.81 (d, J=4.0 Hz, 2H), 8.24 (d, J=8.2 Hz, 1H); $^{13}$C NMR (50 MHz, CDCl$_3$): δ 71.2, 74.3, 125.6, 126.2, 129.9, 134.1, 135.1, 145.9, 154.2

4-(3-nitrophenyl)-1,3-dioxolan-2-one (4p)

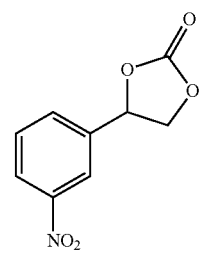 [SMILES: O=C1OCC(c2cccc([N+](=O)[O-])c2)O1]

Yield: 75%; IR: (neat, cm$^{-1}$): u$_{max}$ 1071, 1166, 1349, 1530, 1805; $^1$H NMR (200 MHz, CDCl$_3$): δ 435 (dd, J=8.7, 1.1 Hz, 1H), 4.91 (t, J=8.5 Hz, 1H), 5.81 (t, J=7.8 Hz, 1H), 7.64-7.78 (m, 2H), 8.24-8.33 (m, 2H); $^{13}$C NMR (50 MHz, CDCl$_3$): δ 70.7, 76.3, 120.9, 124.5, 130.5, 131.4, 138.2, 148.6, 153.8

4-(benzo[d][1,3]dioxol-5-yl)-1,3-dioxolan-2-one (4q)

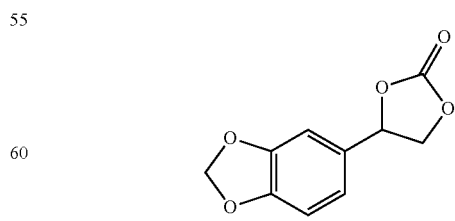

Yield: 86%; IR: (neat, cm$^{-1}$): u$_{max}$ 1070, 1164, 1251, 1505; 1791; $^1$H NMR (200 MHz, CDCl$_3$): δ 4.32 (t, J=8.4 Hz, 1H), 4.75 (t, J=8.5 Hz, 1H), 5.58 (t, J=8.0 Hz, 1H), 6.01 (s, 2H), 6.84 (bs, 3H); $^{13}$C NMR (50 MHz, CDCl$_3$): δ 71.0, 78.0, 101.5, 106.1, 108.6, 120.3, 129.2, 148.5, 148.8, 154.6

4-(3,4,5-trimethoxyphenyl)-1,3-dioxolan-2-one (4j)

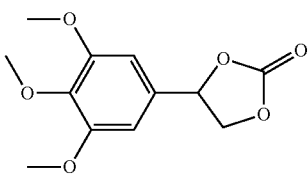 [SMILES: COc1cc(C2COC(=O)O2)cc(OC)c1OC]

Yield: 90%; IR: (neat, cm$^{-1}$): u$_{max}$ 1068, 1125, 1243, 1510, 1796; $^{1}$H NMR (200 MHz, CDCl$_3$): δ 3.84 (s, 3H), 3.88 (s, 6H), 4.31 (t, J=8.3 Hz, 1H), 4.78 (t, J=8.4 Hz, 1H), 5.60 (t, J=7.9 Hz, 1H), 6.54 (s, 2H); $^{13}$C NMR (50 MHz, CDCl$_3$): δ 56.1, 60.7, 71.1, 78.0, 102.6, 131.2, 138.8, 153.8, 154.8, 154.5

4,5-dimethoxy-2-(2-oxo-1,3-dioxolan-4-yl)benzonitrile (4t)

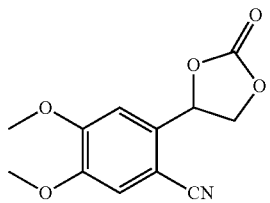 [SMILES: COc1cc(C#N)c(C2COC(=O)O2)cc1OC]

Yield: 83%; IR: (neat, cm$^{-1}$): u$_{max}$ 1064, 1168, 1270, 1516, 1793, 2218; $^{1}$H NMR (200 MHz, CDCl$_3$): δ 2.09 (q, J=7.8 Hz, 1H), 2.82-3.09 (m, 1H), 3.89 (s, 3H), 3.94 (s, 3H), 4.14 (dd, J=8.3, 1.6 Hz, 1H), 4.51 (t, J=8.2 Hz, 1H), 4.67-4.80 (m, 1H), 6.54 (s, 1H), 6.80 (s, 1H), 7.03 (s, 1H); $^{13}$C NMR (50 MHz, CDCl$_3$): δ 29.5, 35.0, 56.1, 69.0, 75.6, 103.0, 112.3, 114.2, 118.0, 138.1, 147.9, 152.9, 154.5

(E)-4-styryl-1,3-dioxolan-2-one (4h)

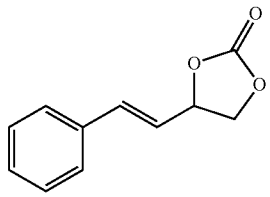 [SMILES: O=C1OCC(/C=C/c2ccccc2)O1]

Yield: 98%; IR: (neat, cm$^{-1}$): u$_{max}$ 1070, 1168, 1648, 1800; $^{1}$H NMR (200 MHz, CDCl$_3$): δ 4.23 (t, J=8.0 Hz, 1H), 4.64 (t, J=8.2 Hz, 1H), 5.26 (q, J=7.9 Hz, 1H), 6.15 (dd, J=15.7, 7.7 Hz, 1H), 6.73 (d, J=15.7 Hz, 1H), 7.30-7.43 (m, 5H); $^{13}$C NMR (50 MHz, CDCl$_3$): δ 69.2, 77.6, 122.4, 126.9, 128.8, 129.0, 134.8, 136.6, 154.4

4-phenethyl-1,3-dioxolan-2-one (4s)

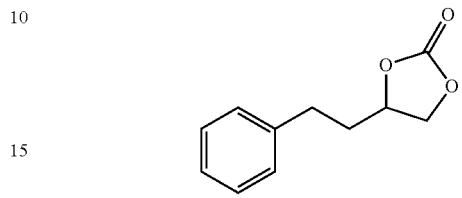

Yield: 77%; IR: (neat, cm$^{-1}$): u$_{max}$ 1061, 1165, 1796; $^{1}$H NMR (200 MHz, CDCl$_3$): δ 1.87-2.24 (m, 2H), 2.65-2.93 (m, 2H), 4.01 (dd, J=8.3, 1.1 Hz, 1H), 4.44 (t, J=8.2 Hz, 1H), 7.15-7.34 (m, 5H); $^{13}$C NMR (50 MHz; CDCl$_3$): δ 30.8, 35.6, 69.1, 75.8, 126.5, 128.3, 128.7, 139.6, 154.6 tert-butyl ((S)-1-((S)-2-oxo-1,3-dioxolan-4-yl)-2-phenylethyl)carbamate (4u)

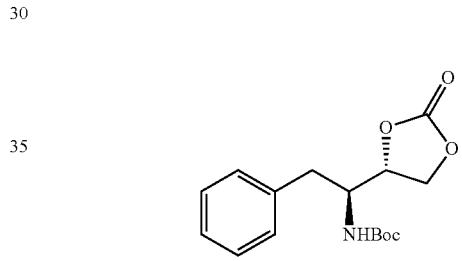

Yield: 79%; IR: (neat, cm$^{-1}$): u$_{max}$ 1061, 1169, 1249, 1366, 1689, 1800; $^{1}$H NMR (200 MHz, CDCl$_3$): δ 1.40 (s, 9H), 2.82-3.05 (m, 2H), 4.09 (m, 1H), 4.28-4.44 (m, 2H), 4.67 (m, 2H), 7.22-7.33 (m, 5H); $^{13}$C NMR (50 MHz, CDCl$_3$): δ 28.2, 38.5, 52.8, 66.5, 76.1, 80.4, 127.1, 128.88, 129.2, 136.4, 154.6, 155.9

4-(2-(benzyloxy)ethyl)-1,3-dioxolan-2-one (4r)

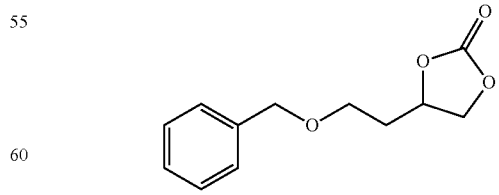

Yield: 80%; IR: (neat, cm$^{-1}$): u$_{max}$ 1061, 1173, 1364, 1454, 1794; 1H NMR (200 MHz, CDCl$_3$): δ 1.99.2.10 (m, 2H), 3.58-3.69 (m, 2H), 4.17 (dd, J=8.4, 1.0 Hz, 1H), 4.47-4.52 (m, 3H), 4.79-4.93 (m, 1H), 7.29-7.40 (m, 5H); $^{13}$C NMR (50

MHz, CDCl$_3$): δ 32.0, 33.9, 61.5, 65.3, 69.1, 69.6, 73.1, 73.3, 75.0, 127.5, 127.8, 128.4, 137.5, 138.0, 154.7

4-vinyl-1,3-dioxolan-2-one (4g)

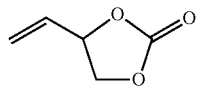

Yield: 65%; IR: (neat, cm$^{-1}$): u$_{max}$ 1060, 1168, 1385, 1805; $^1$H NMR (200 MHz, CDCl$_3$): δ 4.17 (t, J=7.8 Hz, 1H), 4.61 (t, J=8.4 Hz, 1H), 5.12 (dd, J=14.9, 7.5 Hz, 1H), 5.48 (t, J=16.5 Hz, 1H), 5.83-6.0 (m, 1H); $^{13}$C NMR (50 MHz, CDCl$_3$): δ 68.9, 77.1, 121.0, 132.3, 154.3

4-ethyl-1,3-dioxolan-2-one (4c)

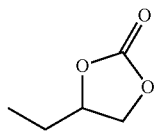

Yield: 65%; IR: (neat, cm$^{-1}$): u$_{max}$ 1060, 1177, 1377, 1797; $^1$H NMR (200 MHz, CDCl$_3$): δ 1.03 (t, J=7.4 Hz, 3H), 1.72-1.87 (m, 2H), 4.1 (dd, J=8.2, 1.5 Hz, 1H), 4.55 (t, J=8.2 Hz, 1H), 4.63-4.73 (m, 1H); $^{13}$C NMR (50 MHz, CDCl$_3$): δ 7.9, 26.2, 68.5, 77.6, 154.6

4-methyl-1,3-dioxolan-2-one (4b)

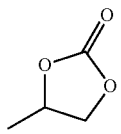

Yield: 40%; IR: (neat, cm$^{-1}$): u$_{max}$ 1051, 1183, 1389, 1793; $^1$H NMR (200 MHz, CDCl$_3$): δ 1.49 (d, J=6.1 Hz, 3H), 4.02 (dd, J=8.2, 1.0 Hz, 1H), 4.55 (t, J=8.0 Hz, 1H), 4.77-4.94 (m, 1H); $^{13}$C NMR (100 MHz, CDCl$_3$): δ 19.0, 70.4, 73.4, 154.8.

4-isopropyl-1,3-dioxolan-2-one (4d)

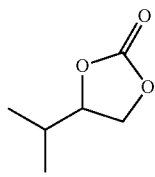

Yield: 73%; IR: (neat, cm$^{-1}$): u$_{max}$ 1075, 1175, 1392, 1789; $^1$H NMR (200 MHz, CDCl$_3$): δ 0.85 (d, J=6.8 Hz, 3H), 1.04 (d, J=6.5 Hz, 3H), 1.86-2.03 (m, 1H), 4.08-4.24 (m, 1H), 4.37-4.53 (m, 2H); $^{13}$C NMR (50 MHz, CDCl$_3$): δ 16.4, 16.8, 31.4, 67.2, 80.9, 154.6.

4-butyl-1,3-dioxolan-2-one (4e)

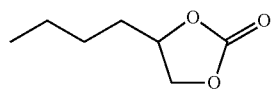

Yield: 89%; IR: (neat, cm$^{-1}$): u$_{max}$ 1066, 1173, 1797; $^1$H NMR (200 MHz, CDCl$_3$): δ 0.88-0.95. (m, 3H), 1.23-1.51 (m, 3H), 1.58-1.85 (m, 3H), 4.05 (dd, J=8.2, 1.0 Hz, 1H), 4.51 (t, J=8.2 Hz, 1H), 4.62-4.76 (m, 1H); $^{13}$C NMR (50 MHz, CDCl$_3$): δ 13.8, 22.2, 26.4, 33.6, 69.3, 76.9, 154.9.

4-hexyl-1,3-dioxolan-2-one (4f)

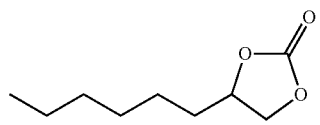

Yield: 94%; IR: (neat, cm$^{-1}$): u$_{max}$ 1065, 1170, 1802; $^1$H NMR (200 MHz, CDCl$_3$): δ 0.86-0.93 (m, 3H), 1.30-1.49 (m, 8H), 1.59-1.84 (m, 2H), 4.06 (t, J=7.2 Hz, 1H), 4.51 (t, J=7.96 Hz, 1H), 4.62-4.76 (m, 1H); $^{13}$C NMR (50 MHz, CDCl$_3$): δ 13.9, 22.4, 24.3, 28.7, 31.4, 33.8, 69.2, 76.8, 154.7; Elemental analysis: C$_9$H$_{16}$O$_3$, Calculated, C, 62.77; H, 9.36. Observed, C, 62.73; H, 9.40%.

ADVANTAGES OF THE INVENTION

1. New synthetic protocol involving readily available starting material
2. Simple reaction procedure using cheap reagents
3. Use of CO$_2$ under atmospheric pressure
4. Easy protocol which is amenable for scale up
5. Metal-free synthesis and milder reaction conditions
6. Novel single step procedure involving Corey-Chaykovsky reaction.

The invention claimed is:

1. One step transition metal free process for the synthesis of cyclic carbonates of formula I from an aldehyde of formula II and Corey-Chaykovsky reagent in presence of carbon dioxide comprising:

Formula II

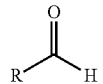

R = alkyl, aryl, vinyl

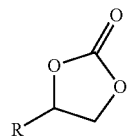

Formula I

R = alkyl, aryl, vinyl a. adding a solvent to NaH followed by stirring under nitrogen at temperature ranging between 0-35° C. for a period ranging between 0.5 to 1 hrs to obtain a slurry;
b. adding Corey Chaykovsky reagent to the slurry of step (a) to obtain a homogeneous solution;
c. adding aldehyde of formula II slowly to homogenous mixture of step (b) followed by bubbling $CO_2$ gas into the reaction mixture with stirring at temperature ranging between 40 to 60° C. for a period ranging between 6 to 8 hrs to obtain cyclic carbonate of formula I.

2. The process according to claim 1, wherein the Corey-Chaykovsky reagent used in step (b) is selected from sulfurylide.

3. The process according to claim 2, wherein the Corey-Chaykovsky reagent is preferably selected from $Me_3SI$ or $Me_3SOI$.

4. The process according to claim 1, wherein NaH used in step (a) was previously washed with petroleum ether to remove mineral oil.

5. The process according to claim 1, wherein the solvent used in step (a) is selected from DMSO or a mixture of DMSO and THF.

6. The process according to claim 1, wherein the solvent is preferably mixture of DMSO and THF in the ratio of 1:1.

7. The process according to claim 1, wherein representative compounds of cyclic carbonate of formula I are
i. 4-Phenyl-1,3-dioxolan-2-one
ii. 4-(2-bromophenyl)-1,3-dioxolan-2-one
iii. 4-(4-fluorophenyl)-1,3-dioxolan-2-one
iv. 4-(4-chlorophenyl)-1,3-dioxolan-2-one
v. 4-(4-(trifluoromethyl)phenyl)-1,3-dioxolan-2-one
vi. 4-Phenyl-1,3-dioxolan-2-one
vii. 4-(2-bromophenyl)-1,3-dioxolan-2-one
viii. 4-(4-fluorophenyl)-1,3-dioxolan-2-one
ix. 4-(4-chlorophenyl)-1,3-dioxolan-2-one
x. 4-(4-(trifluoromethyl)phenyl)-1,3-dioxolan-2-one
xi. 4-(2-methoxyphenyl)-1,3-dioxolan-2-one
xii. 4-(2-nitrophenyl)-1,3-dioxolan-2-one
xiii. 4-(3-nitrophenyl)-1,3-dioxolan-2-one
xiv. 4-(benzo[d][1,3]dioxol-5-yl)-1,3-dioxolan-2-one
xv. 4-(3,4,5-trimethoxyphenyl)-1,3-dioxolan-2-one
xvi. 4,5-dimethoxy-2-(2-oxo-1,3-dioxolan-4-yl)benzonitrile
xvii. (E)-4-styryl-1,3-dioxolan-2-one
xviii. 4-phenethyl-1,3-dioxolan-2-one
xix. tert-butyl ((5)-1-((S)-2-oxo-1,3-dioxolan-4-yl)-2-phenylethyl)carbamate
xx. 4-(2-(benzyloxy)ethyl)-1,3-dioxolan-2-one
xxi. 4-vinyl-1,3-dioxolan-2-one
xxii. 4-ethyl-1,3-dioxolan-2-one
xxiii. 4-methyl-1,3-dioxolan-2-one
xxiv. 4-isopropyl-1,3-dioxolan-2-one
xxv. 4-butyl-1,3-dioxolan-2-on
xxvi. 4-hexyl-1,3-dioxolan-2-one.

8. The process according to claim 1, wherein yield of cyclic carbonate of formula I is in the range of 40-98%.

* * * * *